United States Patent [19]
Masson et al.

[11] Patent Number: 5,863,730
[45] Date of Patent: Jan. 26, 1999

[54] PROCEDURE FOR THE POLYMERIZATION OF NUCLEIC ACID SEQUENCES AND ITS APPLICATIONS

[75] Inventors: Jean-Michel Masson; Florence Boe, both of Toulouse, France

[73] Assignee: Centre National de la Recherche Scientifique - CNRS, Paris, France

[21] Appl. No.: 714,357

[22] Filed: Sep. 16, 1996

[30] Foreign Application Priority Data

Sep. 15, 1995 [FR] France .................................. 95 10872

[51] Int. Cl.$^6$ .............................. C12Q 1/68; C12P 21/00; C12N 15/63; C07H 21/04
[52] U.S. Cl. ............................ 435/6; 435/69.1; 435/91.1; 435/172.3; 536/22.1; 536/23.1; 536/24.3; 536/24.31; 536/24.32; 536/24.33
[58] Field of Search ........................... 435/6, 172.3, 69.1, 435/252.3, 320.1, 91.1; 536/22.1, 23.1, 24.3, 24.31, 24.32, 24.33

[56] References Cited

U.S. PATENT DOCUMENTS

| | | | |
|---|---|---|---|
| 4,403,036 | 9/1983 | Hartley et al. | 435/317 |
| 5,093,251 | 3/1992 | Richards et al. | 435/172.3 |

FOREIGN PATENT DOCUMENTS

| | | |
|---|---|---|
| WO 88/05082 | 7/1988 | WIPO . |
| WO 90/05177 | 5/1990 | WIPO . |

OTHER PUBLICATIONS

Molecular Cloning, A Laboratory Manual, Second Edition, 1989, pp. 1.6 and 1.19, J. Sambrook, et al., "Plasmid Vectors".

Lobel et al, "Construction of mutants of Moloney murine leukemia virus by suppressor–linker insertional mutagenesis: positions of viable insertion mutations", Proc. Natl. Acad. Sci. 81:4149–4153, Jul. 1984.

Taylor et al, "A general method for cloning DNA fragments in multiple copies", Gene 53:139–144, 1987.

Graham et al, "A rapid and reliable method to create tandem arrays of short DNA sequences", Biotechniques 13(5):780–789, 1992.

Hwang et al, "A method of cloning multiple direct repeats of a DNA segment", Biotechniques 14(5):766–767, 1993.

*Primary Examiner*—W. Gary Jones
*Assistant Examiner*—Jeffrey Fredman
*Attorney, Agent, or Firm*—Oblon, Spivak, McClelland, Maier & Neustadt, P.C.

[57] ABSTRACT

This procedure comprises the following steps: (1) cleavage of a circular cloning vector comprising two restriction sites a and b giving cohesive ends which are compatible with one another, and two restriction sites c and d which are close to the restriction sites a and b, by restriction enzyme(s), (2) introduction by ligation of the nucleic acid sequence to be polymerized into the linearized vector obtained in (1), between the two restriction sites a and b (1x vector), (3) cleavage of the recircularized vector obtained in (2), by restriction enzyme(s), (4) introduction by ligation of a gene coding for a suppressor tRNA into the linearized vector obtained in (3), between the two restriction sites c and d (1x+s vector), (5) cleavage of the vector obtained in (4) by restriction enzyme(s), (6) introduction by ligation of the fragment a-d obtained in (5) (1x+s fragment) between the sites b and d of a 1x vector as obtained in (2), after cleavage of this 1x vector at the said sites b and d, (7) introduction by ligation of the fragment obtained in (6) (2x+s fragment) between the sites b and d of a 1x vector as obtained in (2), after cleavage of this 1x vector, the cleavage being as defined in (6), (8) repetition of step (7), by insertion of the nx+s fragment into a 1x vector, until a sequence containing n+1 fragments is obtained, (9) transformation of a bacterial strain with the vector obtained in (8), and selection of mut+ strains, and (10) extraction of the (n+1)x polymer from the said selected strains.

17 Claims, 5 Drawing Sheets

```
                                                           XhoI
5'  TCGACTATGGGCGCAGCGTCAATGACGCTGACGGTACAGGCC         3'
        GATACCCGCGTCGCAGTTACTGCGACTGCCATGTCCGGAGCT
    SalI
```

PROCEDURE FOR THE POLYMERIZATION OF NUCLEIC ACID SEQUENCES AND ITS APPLICATIONS

The present invention relates to a procedure for the polymerization of nucleic acid sequences as well as to its applications, in particular as nucleic acid (for example DNA) size marker, for the construction of genes coding for highly repetitive proteins and for the inclusion of repeated nucleic acid sequences, and more especially those of DNA, in vectors or genomic sequences.

A number of methods exist for the production of nucleic acid in large amounts from small amounts of samples of nucleic acid; there may be mentioned especially:

methods for the cloning of a nucleic acid sequence in a suitable system, in which a nucleic acid sequence is inserted into a vector which is used to transform a suitable host cell. When the host cell is cultured, the vector is replicated, and a large number of copies of the desired nucleic acid sequence are consequently produced (Sambrook J. et al., *Molecular cloning: a laboratory manual,* 2nd ed., 1989, Cold Spring Harbor Laboratory).

in vitro amplification methods such as PCR (polymerase chain reaction) (Saiki et al., Science, 1985, 230, 1350–1354).

However, these methods are not suitable for obtaining repetitive polymers of a double-stranded DNA sequence of any given size (from a few tens of nucleotides to a few thousand nucleotides). In addition, the obtaining of repetitive polymers of a nucleic acid sequence by in vitro polymerization, followed by the separation of the sequences in accordance with their size, with or without restriction cleavages or by methods derived from PCR, proves especially intricate and difficult to carry out industrially.

Consequently, it was the aim of the present application to provide for a procedure for the amplification of nucleic acid sequences, independent of the size or nature of the sequence, whereas the methods referred to above entail limitations associated either with the nature of the sequence or with the size of the fragment to be amplified.

The subject of the present invention is a procedure for the amplification or polymerization of a nucleic acid sequence, in particular a double-stranded DNA sequence, by a cloning method, which procedure is characterized in that it essentially comprises the following steps:

(1) cleavage of a circular cloning vector comprising two restriction sites a and b giving ends which are compatible with one another, and two restriction sites c and d which are close to the restriction sites a and b, by means of at least one restriction enzyme capable of performing the said cleavage at the sites a and b; for the purposes of the invention, close is understood to mean the fact that the sites c and d must be on the same side of a or b, at a distance of at least 6 base pairs, and preferably a few tens of base pairs, from a or b; in fact, there is no maximum distance imposed by the method, (2) introduction by ligation of the nucleic acid sequence to be polymerized into the linearized vector obtained in (1), between the two restriction sites a and b (obtaining of the 1x vector, that is to say containing a single copy of the sequence to be polymerized), (3) cleavage of the recircularized vector obtained in (2), by means of at least one restriction enzyme capable of performing the said cleavage at the restriction sites c and d, (4) introduction by ligation of a gene coding tor a suppressor tRNA into the linearized vector obtained in (3), between the two restriction sites c and d (obtaining of the 1x+s vector, containing a single copy of the sequence to be polymerized and the gene coding for a suppressor tRNA), and selection of the clones carrying the 1x+s insert in the correct orientation, by transformation of suitable bacteria, (5) cleavage of the vector obtained in (4) by means of at least one restriction enzyme capable of performing the said cleavage at the sites a and d, (6) introduction by ligation of the fragment a-d obtained in (5) (1x+s fragment) between the sites b and d of a 1x vector as obtained in (2), after cleavage of this 1x vector by means of at least one restriction enzyme capable of performing the said cleavage at the said sites b and d (obtaining of the 2x+s vector), and selection of the clones carrying the 2x+s insert in the correct orientation, by transformation of suitable bacteria, (7) introduction by ligation of the fragment obtained in (6) (2x+s fragment) between the sites b and d of a 1x vector as obtained in (2), after cleavage of this 1x vector, the cleavage being as defined in (6) (obtaining of the 3x+s vector): the obtaining of the 3x polymer is hence done in the same manner as in step (6), by introducing the 2x+s fragment into the 1x vector, (8) repetition of step (7), by insertion of the nx+s fragment last obtained into a 1x vector, until a sequence containing n+1 fragments identical to the nucleic acid sequence to be polymerized is obtained, (9) transformation of a bacterial strain with the vector obtained in (8), which bacterial strain contains a mutation (mut$^-$) at least in an essential gene, preferably both in an essential gene and in a reporter gene, such that its growth is possible only in the presence of the said suppressor tRNA (that is to say in the presence of the nx+s vector), and selection of the strains displaying the mut$^+$ character, and (10) extraction of the (n+1)x polymer from the said selected strains.

One cloning cycle entails the insertion of an nx+s sequence (with $n \geq 2$) into a 1x vector; in each of these cycles, the joining between the nx+1 and 1x fragments via the compatible ends of the sites a and b is such that only the sites a and b at the ends of the new polymerized (n+1)x fragment actually remain in existence.

The procedure according to the present invention has a number of advantages:

it enables any nucleic acid sequence to be amplified or polymerized (procedure independent of the nature of the DNA sequence to be polymerized); this is especially advantageous for producing molecular weight markers whose migration conforms perfectly to the physicochemical laws (no defect of migration associated with the sequence) whereas, with the methods of the prior art described above, there is often an imbalance in the representation of bands of different sizes;

it is especially well suited to the polymerization of small fragments which are often difficult to clone by the conventional methods; this is especially important as regards size markers for PCR.

As an example, the procedure according to the invention makes it possible, in particular, to polymerize sequences of natural or synthetic origin such as the sequences coding for highly repetitive proteins, the sequences for regulation or interaction with proteins that bind to DNA or RNA, of viral or cellular origin (binding sites of the activators or repressors of gene expression, prokaryotic or eukaryotic origins of replication).

According to the invention:

the restriction sites are preferably selected, as regards the restriction sites a and b, which are preferably different and have compatible ends, from all the sites corresponding to enzymes that cut DNA with blunt ends (Pvu II, Eco RV, Hinc II, Sma I, Sna BI, Ssp I, and the like), and the cleavage sites of enzymes that give cohesive ends which are compatible but whose fusion does not regenerate a site which can be recut by one of the two enzymes (hence not enzymes with a four-base recognition site), such as Eco RI and Mun I; Apa LI and Sfc I; Bam HI and Bcl I, Bgl II or Bst YI; Sal I and Xho I; Nco I and Bsp HI or Afl III; Xma I and Age I; Ngo MI and Bsp EI; Xba I and Nhe I, Avr II or Spe I; Bss HII and Mlu I or Dsa I; Bst BI and Cla I, Acc I, Nar I or Psp 1406 I; Pst I and Nsi I;

as regards the restriction sites c and d, which are preferably different from the sites a and b, from any restriction site, provided it is not included in the sequence of the suppressor tRNA; as a variant, the site b and the site c merge;

the said suppressor tRNA is selected from ochre, opal, frameshift or amber suppressor tRNAs, preferably from an amber suppressor tRNA (J M Masson et al., Gene, 1986, 179–183; L G Kleina et al., J. Mol. Biol., 1990, 213, 705–717; J. Normanly et al., J. Mol. Biol., 1990, 213, 719–726; J. Normanly et al., Proc. Natl. Acad. Sci. USA, 1986, 83, 6548–6552);

the said bacterial strain is preferably an *Escherichia coli* strain carrying an amber mutation both in an essential gene (for example argE) and in a reporter gene (for exalmple lacZ).

The procedure according to the invention also includes the case where the starting fragment is already a polymerized fragment, the term 1x in this case meaning: "one unit to be polymerized".

As a variant, the bacterial strain, and in particular the *E. coli* strain, is, in addition, recA, that is to say deficient for homologous recombination; in effect, the construction of this kind of polymer in *E. coli* may give rise to recombination and deletion phenomena, especially when n>10.

According to the invention, the effect of the suppressor-selected strain pair is that, when, at the end of a cloning, a colony grows on arginine-free medium and is blue, there can be no doubt that the recombinant in question is the correct one, and hence that the insert in question is the correct one, since it is the insert which is the carrier of the selectable marker.

Such a procedure finds application in particular:

1) In the preparation of DNA size markers: the polymerization of a DNA sequence lying between two restriction sites, as is described above, enables regular ladders of DNA molecules to be constructed. These ladders are used as size "markers" during the migration of DNA fragments originating from sequencing or from a restriction analysis.

To obtain such a ladder, it suffices to combine the n vectors each carrying a defined number of copies of the initial sequence (from 1 to n), and to cut them all with the two compatible enzymes a and b which flank the polymerized sequence.

As a variant, it is possible to carry out the cleavage of the different vectors separately, and then to mix the products originating from the different cleavages.

The advantage of this method is that the different components may be assayed so that some bands are over-represented relative to the whole (for example the bands of 500, 1000 and 1500 bp in a ladder with a spacing of 100), which will provide an internal size reference point.

Another advantage of the method is that it is possible in this way to construct ladders of the size which is desired, to within one base. It is also possible to make ladders not containing all the components of a series (100, 200, 400, 500, 700, 900, 1000, and the like), which is possibly more readable.

2) In the construction of genes coding for highly repetitive proteins. A number of highly repetitive proteins have important potential biotechnological applications. This applies to collagens, silks, keratin, elastin and numerous adhesion proteins or repetitive unnatural proteins.

3) The inclusion of repeated DNA sequences in vectors or genomes: such sequences may serve as labels to isolate, characterize or purify DNA fragments by interaction with other nucleotide sequences or with proteins that bind specifically to these sequences. Such sequences are also especially suitable for the synthesis and use of sequences regulating the transcription of genes in eukaryotic expression systems.

Besides the foregoing provisions, the invention also comprises other provisions which will become apparent from the description which follows, which refers to examples of implementation of the procedure which is the subject of the present invention as well as to the attached drawings, in which:

FIGS. 1 and 2 illustrate the procedure for the polymerization of nucleic acid sequence, according to the invention; FIG. 1: general procedure; FIG. 2: application of said procedure to an RRE sequence in a BSKS plasmid.

The outline of the method is as follows (FIG. 1): the sequence to be polymerised is first cloned between two compatible ends restriction sites in a cloning vector (sites A and B), generating vector 1X. Then, a small cassette encompassing an amber suppressor tRNA gene with its promoter and transcription terminator is cloned next to it (between sites C and D), to obtain vector 1X+S which is used to transform an amber mutated strain, such as, for example, XAC-1. The 2X+S vector is obtained by cutting out the 1X+S fragment with restriction enzymes A and D, and cloning it between sites B and D of vector 1X. Growth of the transformants on minimal medium ensures that only the correct construct is selected for.

Figure 1:
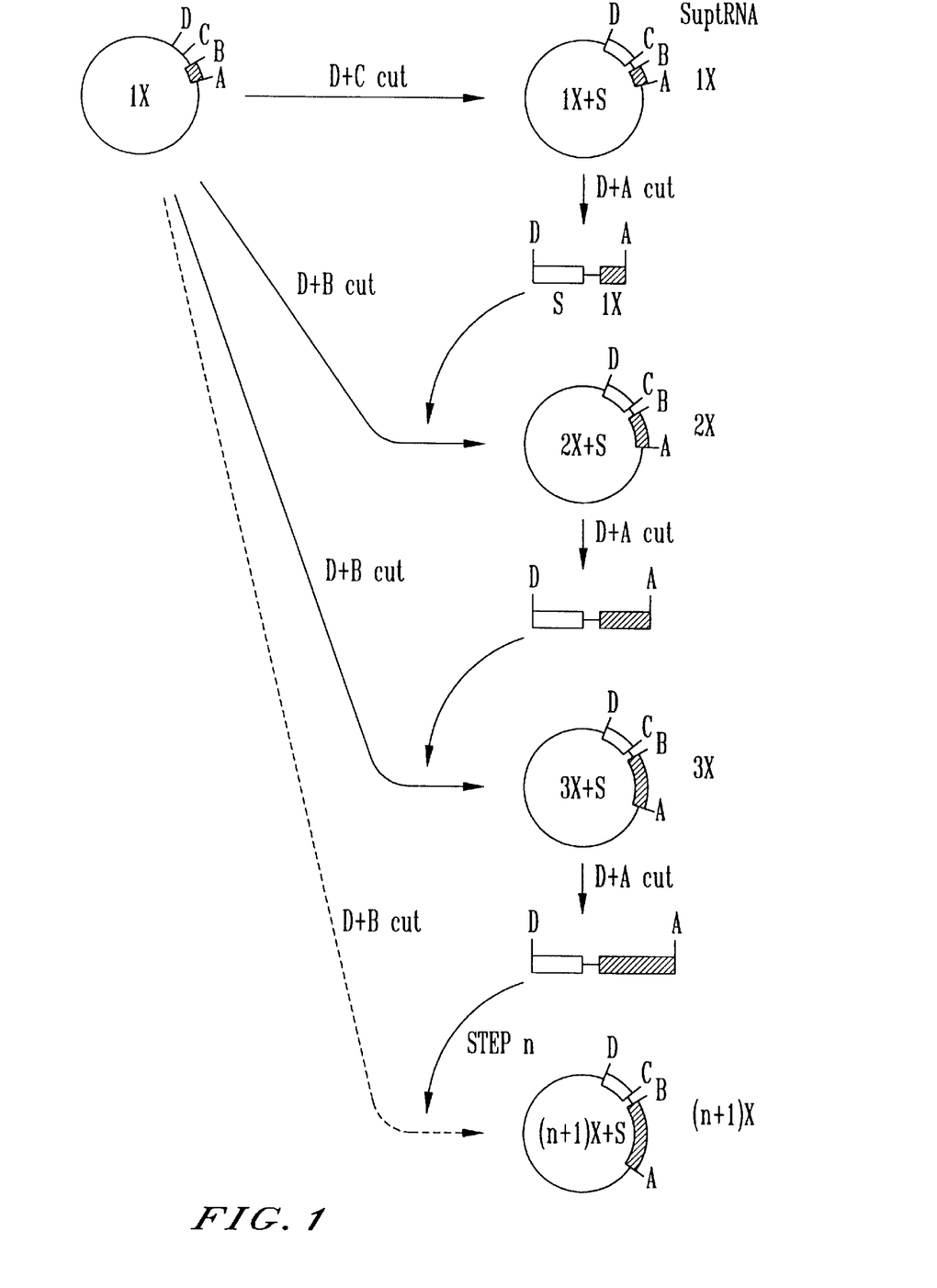

In the same manner, the 3X+S vector is obtained by cloning the 2X+S A/D fragment into the 1X vector between the B and the D sites and selecting the transformants for the presence of the suppressor gene. The 3X+S vector will thus contain three adjacent copies of the sequence of interest, in the same orientation, between two unique restriction sites A and B, as the sites between the copies are destroyed by the cloning procedure and the asymmetrical cloning ensures that only one orientation of the sequence is inserted. Each time the cloning step is repeated, one unit of the sequence is added to the polymerised sequence.

It should be clearly understood, however, that these examples are given only by way of illustration of the subject of the invention, and in no way constitute a limitation of the latter.

EXAMPLE 1

Implementation of the Procedure for Preparing a Polymeric Sequence Based on the Target RNA Sequence for Rev, the RRE: Obtaining of the Polymeric Sequence RRE6x in an *E. coli* Strain XAC-1

A. Materials

RRE sequence:

The RRE is a sequence of 234 nucleotides, present in the env gene of the HIV-1 virus, capable of forming an RRE structural RNA (M. H. Malim et al., Nature, 1989, 338, 254–257).

Figure 3:
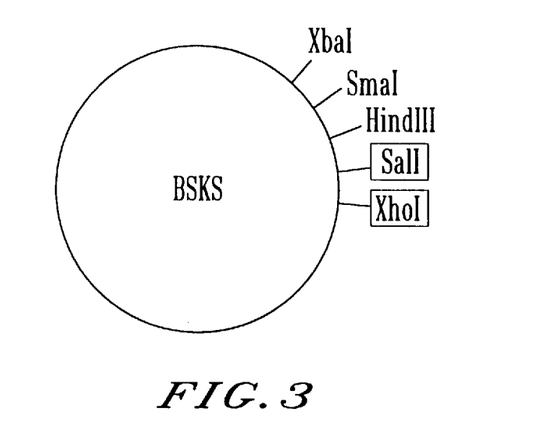
FIG. 3 shows the BSKS plasmid.

BSKS plasmid (see FIG. 3):

This is marketed by the company Stratagène under the name pbluescript KS+.

*E. coli* strain XAC-1:

This is described, in particular, in the publication in the name of J M. Masson et al. (Gene, 1986, 47, 179–183).

Gene for the suppressor tRNA$^{Phe}$ of *E. coli:*

The construction of this gene is described in J. Normanly et al. (Proc. Natl. Acad. Sci. USA, cited above).

B. Methods

Figure 5:
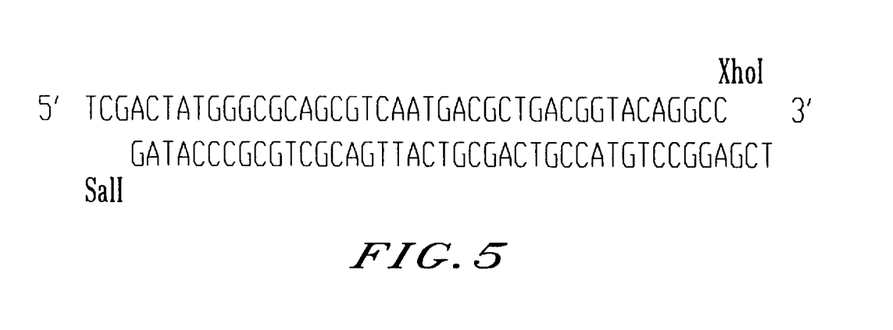
FIG. 5 shows the hybridization of the oligonucleotides RRE1xa(SEQ ID NO:1) and b(SEQ ID NO:2) to form the minimal binding component of the RRE.

Construction of the minimal sequence RRE1x (see FIG. 5):

The purified oligonucleotides (5'→3' direction) RRE1xa (TCGACTATGGGCGCAGCGTCAATGACGCTGACGG TACAGGCC) (SEQ ID NO:1) and RRE1xb (TCGAGGCC TGTACCGTCAGCGTCATTGACGCTGCGCCCATAG) (SEQ ID NO:2) are phosphorylated and then hybridized with one another according to the protocols below.

Synthesis and purification of the oligonucleotides:

The oligonucleotides are synthesized on an Applied Biosystem synthesizer according to the phosphoramidite method. Not detritylated after synthesis, they are lyophilized and then purified on NENsorb prep® disposable columns (DuPont Co.) according to the manufacturer's protocol. The tritylated oligonucleotides are thus retained selectively on the column, and they are then eluted after an acid hydrolysis (0.5% (w/v) TFA) of the trityl function. After a further lyophilization, they are taken up with TE buffer (10 mM Tris-HCl, pH 8, and 1 mM EDTA). The concentrations for the solutions obtained are determined by measuring the absorbance at 260 nm, given that an absorbance of one unit corresponds to 37 μg of DNA.

Phosphorylation:

The reaction medium, of final volume 20 μl, contains 2 μg of oligonucleotide, 70 mM Tris-HCl buffer, pi 7.6, 0.75 mM ATP, 10 mM magnesium chloride, 5 mM DTT and 5 units of phage T4 phosphonucleotide kinase (PNK).

After incubation for one hour at 37° C., the enzyme is inactivated by incubation at 65° C. for 10 minutes.

In the case of radioactive hybridizations, the added group contains $^{32}$P. In this case, 30 pmol of oligonucleotide are phosphorylated (given that 0.1 μg=250/L in pmol with L=length of the oligonucleotide) in 10 μl of 25 mM Tris-HCl buffer, pH 7.6, 6 mM MgCl$_2$, 2.5 mM DTT containing 2 μl of [γ-$^{32}$P]ATP (specific activity>5,000 Ci/mmol) and 4 U of polynucleotide kinase. After thermal denaturation of the enzyme, the excess radioactive ATP is removed by ethanol precipitation. The efficiency of incorporation of $^{32}$P is then verified by counting by means of a scintillation counter (Packard Liquid Scintillation Analyser).

Hybridization of the oligonucleotides with one another:

2 μl of each phosphorylated oligonucleotide are incubated for 10 min at 80° C. in a final volume of 20 μl of 100 mM NaCl. Hybridization is then obained by slow cooling to room temperature.

Preparation of plasmid DNAs and cloning techniques:

The general techniques of analysis and cloning of DNA are those described by Maniatis et al. (1982). The extraction of plasmid DNA was performed according to the alkaline lysis method. Restriction enzymes (Pharmacia, BRL, Appligene, Eurogenthec) are used according to the suppliers' recommendations.

For the clonings, the DNA fragments obtained after enzymatic digestions are separated on TAE low melting agarose gel (Seaplaque®, Nusieve) and then extracted on a resin (Magic® prep kit). Linearized vectors having the possibility of closing up on themselves are dephosphorylated by alkaline phosphatase treatment. The phosphatase used is *E. coli* alkaline phosphatase at a concentration of 140 U/ml, marketed by Pharmacia.

This enzyme is stored in water or in its reaction buffer (50 mM Tris-HCl, pH 8, 1 mM ZnCl$_2$).

The DNA to be dephosphorylated is resuspended in 50 μl of reaction buffer and incubated for 30 min at 60° C. The reaction is stopped by adding 0.1% SDS and 100 μg/ml of proteinase K for 50 min at 37° C. The DNA is then extracted with phenol, precipitated and taken up in 20 μl of sterile water. Cloning is carried out by mixing 4 μl of dephosphorylated vector and 10 μl of the double-stranded fragment RRE1x in the presence of one Weiss unit of T4 ligase and its buffer (10 mM DTT, 50 mM Tris-HCl, pH 7.6, 10 mM MgCl$_2$, 1 mM ATP).

Incubation of the ligation mixture is performed overnight at 16° C. Transformation of competent cells is carried out by electroporation according to Dower W J. et al. (NAR, 1988, 16, 6127–6145).

The formation of the double-stranded RRE1x reveals a SalI restriction site (restriction site b according to the invention) at the 5' end, and an XhoI site (restriction site a according to the invention) at the 3' end. This hybridization mixture is incubated with the BSKS plasmid linearized with these same enzymes, in the presence of ligase.

Detection of clones carrying the RRE1x insert: radioactive hybridization on colonies:

After transformation into TG1, the different clones are analysed in order to select those which actually possess the insert corresponding to RRE1x, of 42 bp.

This cloning is verified by in situ hybridization, performed on the different clones obtained, by means of a radioactive probe composed of the oligonucleotide RRE1xb labelled with $^{32}$P at the γ position.

During the cloning of the 42-bp synthetic fragment RRE1x into BSKS, screening is carried out by in situ hybridization according to the method of Grunstein and Hogness (1975).

After transformation of the strain TG1 with the ligation product obtained above and plating on selective medium, one hundred colonies obtained are picked out onto dishes and cultured overnight at 37° C. A nylon membane (Pall Biodyne® A, diameter=85 mm) is applied to the dish.

After 3 to 5 min of adsorption, the membrane is removed and applied to Whatman® paper, in order to dry it, for 30 min at room temperature. The membrane is then applied to the surface of a denaturing solution of 0.5M NaOH (1 to 3 minutes), and thereafter immersed successively in a 1M Tris, pH 7.5, 1.5M NaCl and 0.5M Tris, pH 7.5, 1.5M NaCl solution. It is then dried gently between two sheets of absorbent paper, and the DNA is thereafter fixed for two hours under vacuum at 80° C. or 10 seconds with Crosslinker.

The probe is obtained by labelling the oligonucleotide RRE1xa. The oligonucleotide is radiolabelled by phosphorylation (with T4 polynucleotide kinase and [γ-$^{32}$P]ATP). Hybridization is performed by adding the probe, in the proportion of $10^6$ cpm/ml of hybridization mixture, overnight at a defined temperature. This temperature is calculated according to the empirical relationships established by Lathe R. (J. Mol. Biol., 1985, 183, 1–12) namely:

θ2XSSC(°C.)=94–820/L-1.2.(100-H) with H=100(L-M)/L

L: length of the oligonucleotide,

H: sequence homology between the probe and the DNA,

M: number of unpaired bases.

The filter is then washed for 5 minutes with a solution containing SSC2x, 0.1% SDS, with stirring at room temperature, in order to remove probe which is not fully paired (SSC20x is a solution containing 173.5 g/l of NaCl and 8.2 g/l of sodium citrate adjusted to pH 7 with 10N sodium hydroxide solution).

Visualization is carried out by autoradiography overnight at −80° C. (Kodak film).

Figure 6:
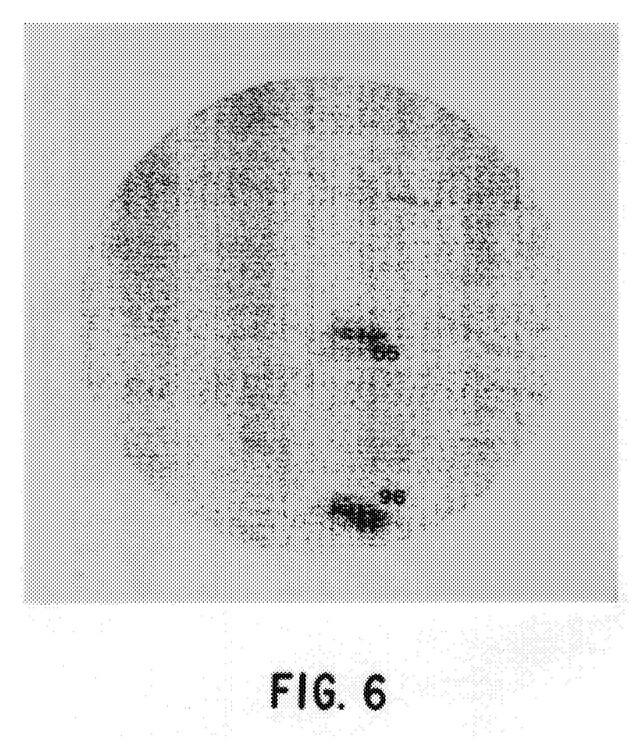
FIG. 6 shows the clones 55 and 96 on an autoradiographic film.

Results:

Of 100 clones analysed in this way, two respond to the probe and hence contain the 42-bp insert. These are the clones 55 and 96 (see FIG. 6), appearing on the autoradiographic film. This presence of the insert was verified by the loss of the NdeI site located between the two cloning sites. Since SalI and XhoI restriction sites are compatible, this suggests that the 98 negative clones correspond to the recircularized form of the BSKS plasmid opened with these enzymes.

Figure 2:
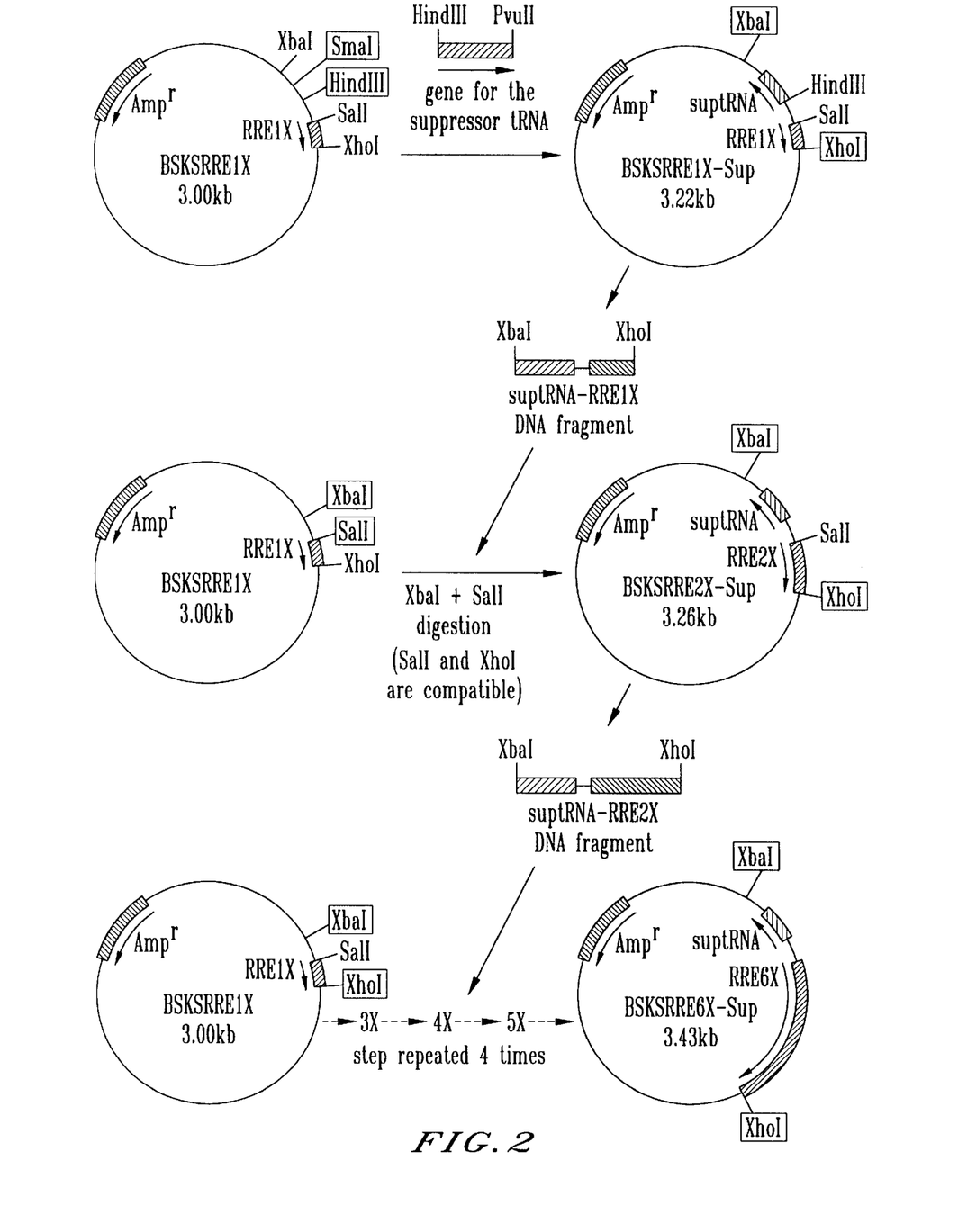

Only the orientation enabling the restriction sites to be recreated is acceptable. After digestion of the two positive clones with the enzymes used for the cloning, SalI and XhoI, only the clone 96 possesses the correct orientation. This clone, designated BSKS-RRE1x, illustrated in FIG. 2, is the starting point for the polymerization of RRE.

Polymerization of RRE1x

To facilitate the obtaining of the different polymers, the vector BSKS-RRE1x was modified by the addition of a DNA fragment which carries a new selectable feature.

This DNA fragment is the gene for a suppressor tRNA$^{Phe}$ of E. coli, which is essential for suppression of the amber mutation carried by an E. coli strain XAC-1.

This mutation affects a gene, ArgE, coding for an enzyme of arginine metabolism. Without the suppression of this mutation and without adding arginine to the culture medium, the strain XAC-1 (mut$^-$) cannot survive. In effect, this suppressor tRNA recognizes the amber codon of the ArgE gene, supplying a phenylalanine residue instead of it in the protein sequence, thus restoring the wild-type form of the enzyme.

Figure 4A:
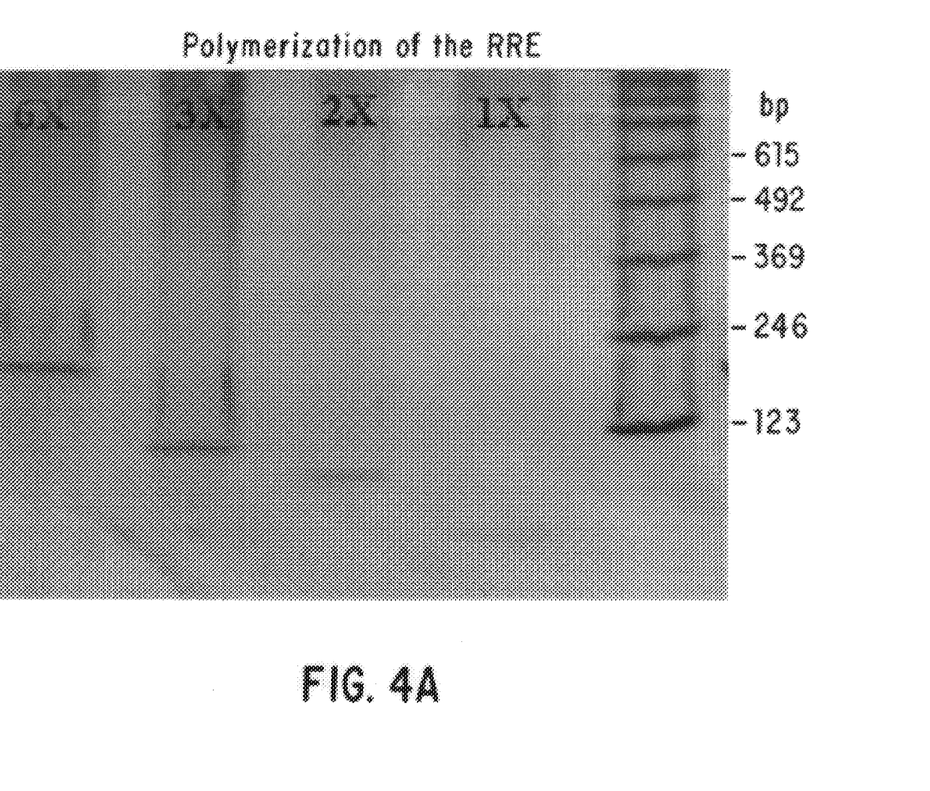
FIGS. 4A and 4B show the result of the polymerization of the RRE, after cleavage with the enzymes Sal I and Xho I and SDS-acrylamide gel electrophoresis (acrylamide gradient 8–25%) followed by silver nitrate staining.
Figure 4B:
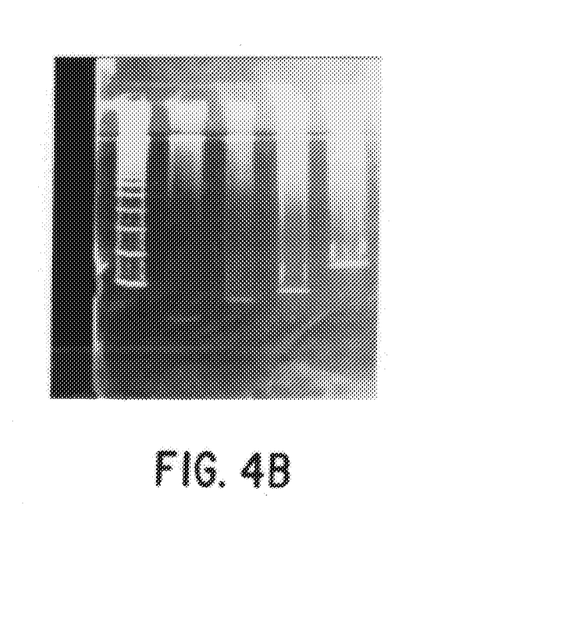

The gene for the suppressor tRNA$^{Phe}$ of E. coli is obtained from the vector pGFIB-1, by the action of the enzymes PvuII and HindIII. This 270-bp fragment is inserted into the vector BSKS-RRE1x, upstream of RRE1x, by means of the SmaI and HindIII restriction sites. Since PvuII and SmaI sites are not compatible, the insertion is verified by cleavage with XbaI (site d) and HindIII (site c), generating an approximate fragment of 280 bp. The XbaI-XhoI fragment containing RRE1x and the suppressor (1x+s fragment) is introduced into the unmodified BSKS-RRE1x vector (clone 96) opened with the restriction enzymes XbaI (side d) and SalI (site b). This cloning permits the insertion of a further copy of RRE1x, adjacent to the first copy of RRE1x (see FIG. 2), to form the vector BSKS-RRE2x+s. This method of construction is repeated on the plasmid BSKS-RRE2x to form BSKS-RRE3x, and so on, until the vector BSKS-RRE6x is produced (see FIG. 2). The presence of the 6x polymer is verified by sequencing and by electrophoresis (FIG. 4) from BSKS-RRE6x.

The presence of the E. coli suppressor as selection pressure enables 100% of clones having the desired construction to be obtained at each step of cloning, after transformation of the E. coli strain XAC-1 (argE, lacZ$_{am}$) obtained. The suppression of the mutation of the amber codon present on the LacZ gene brings about the production of an active β-galactosidase, which enables blue colonies to appear on a medium containing the indicator X-gal (5-bromo-4-chloro-3-indolyl β-D-galactopyranoside); the suppression of the mutation of the amber codon on the ArgE gene brings about the appearance of the Arg$^+$ phenotype.

FIG. 2 illustrates the different steps of polymerization and the different polymers obtained (1x, 2x, 3x and 6x).

EXAMPLE 2

Implementation of the Procedure for Preparing a Polymeric Sequence Based on the Target RNA Sequence for Rev, the RRE: Obtaining of the Polymeric Sequence RRE6x in an E. coli Strain XAC-1recA The procedure is as in Example 1; however the vector RRE6x+s is used to transform an E. coli strain XAC-1 recA.

Introduction of the recA mutation into the XAC-1 strains of E. coli makes it possible to prevent recombination events from interferring with the selection, in accordance with the following protocol;

Transduction:

In order to avoid any recombination phenomenon during the polymerization of the RRE, the strain XAC-1 was modified and rendered recA$^-$ by transduction with the recA$^-$ phage P1.

Not only can bacterial genes be transferred by conjugation or by transposition, they can also be transported passively from one bacterium to another by phage particles, this process being called transduction. This takes place when a viral particle (a transducing phage) accidentally encapsulates portions of the host's chromosome. In the present case, the chromosomal portion affected is the one carrying the fragment deleted from the recA gene in combination with the Srl gene (necessary for the utilization of sorbitol) containing a transposon conferring on it resistance to tetracycline. When the transducing phage attaches itself to a host cell, the fragment of bacterial chromosome is injected into this cell. This fragment can then undergo a crossing over with the host chromosome. When this transducing phage (phage P1) is cultured on a strain genetically different (recA$^+$) from the strain subsequently infected (recA$^-$) by the phage, the formation of a genetically transformed (recA$^-$) bacterium can be the outcome. The segment of the bacterial chromosome carried by a single transducing particle is relatively short, so that only the genes very close to one another will be included in the same transducing particle. Accordingly, this newly formed recA$^-$ strain is selected on selective medium to which tetracycline is added. This recA$^-$ phenotype may be verified by the considerable sensitivity of the strain to UV.

Preparation of recA$^-$ phage P1:

The recA$^-$ donor strain is cultured in 5 ml of LB overnight at 37° C. The culture is diluted, so as to obtain an OD$_{578}$ of between 0.05 and 0.1, in 5 ml of LB with the addition of 0.2% of glucose and 25 µl of 1M CaCl$_2$, then distributed in three flasks and agitated or 30 minutes at 37° C. 75 µl of phage P1 stock are added to the first flask and 150 µl to the second, while the third serves as control. The infected culture is returned to 37° C. until lysis is complete (2 to 3 hours). The phage DNA is purified by adding 100 µl of chloroform to the flasks, and the mixture is agitated vigorously and centrifuged for 10 minutes at 8,000 rpm at 4° C. The supernatant constitutes the stock of recA⁻ phage P1 for the transduction.

Infection of a recA⁺ strain with the recA⁻ phage P1:

The recipient XAC-1 (recA⁺) strain is cultured in 5 ml of LB overnight at 37° C. After centrifugation for 10 minutes at 8,000 rpm, the pellet is taken up in 10 ml of MC buffer (0.1M MgSO₄; 5 mM CaCl₂) and incubated for 10 minutes at 37° C. with agitation. 100 μl of cells prepared in this way are mixed with 100, 10 or 1 μl of recA⁻ phage P1 stock prepared above; a tube containing only cells serves as control. 20 minutes in an incubator suffices for absorption of the phages. 200 μl of 1M sodium citrate are added to the tubes followed by 2.5 ml of top agar. The mixture is poured rapidly onto dishes containing the antibiotic corresponding to the selectable marker carried by the phage (tetracycline). The dishes are left in the incubator for 48 hours at 37° C.

EXAMPLE 3

Construction of Regulatory Sequences for Controlling the Expression of Eukaryotic Genes The procedure according to Example 1 or Example 2 is carried out in order to construct a sequence comprising a number of repetitions of a series of short sequences (regulatory sequences), replacing the RRE sequence by one of the sequences mentioned below; in effect, a large number of eukaryotic genes may be controlled by the addition, upstream of the gene, of a series of short sequences repeated in tandem, the number of repeats determining the level of control of the gene. This applies, for example, to the sequences recognized by the GAL4 regulatory factor in yeast, which form part of the features generally known as upstream activating seqences (UAS). In mammalian cells, a very large number of regulatory sequences are found which are repeated (often 3 or 4 times) upstream of the promoter sequence. For example, the sequence (GGGACTTTCCGC) binding the factor NF-KB, the sequences binding the factors AP1, Sp1, COUP, USF and the like.

The procedure according to the invention enables such repeat sequences to be obtained in a simple manner.

EXAMPLE 4

Genes for Repetitive Proteins: Example of Gelatin

The procedure according to Example 1 or Example 2 is carried out in order to construct a sequence comprising n repetitions of a gene combining several sequences coding for tripeptides, replacing the RRE sequence by one of the sequences mentioned below.

There are two cases in point:

the first relates to genes coding for proteins such as silk, keratin or collagen and gelatin. The sequences are short ones coding for 3 to 6 amino acids and which are highly repeated or semi-repeated.

For example, gelatin consists of chains of amino acids of the type (Gly-X-Pro) n times which endow it with its particular plastic and physicochemical properties. The synthesis of a gene combining several sequences coding for different tripeptides (Gly-Ala-Pro), (Gly-Asp-Pro), (Gly-Val-Pro), and the like, repeated n times, may be otained by the procedure according to the invention. The protein thus obtained then constitutes a gelatin having novel properties, which finds specific applications in both photography and surgery.

another case in point: some proteins contain short repeated segments which generally have as their function adhesion to a tissue or to a particular structure. It is possible to use fragments of genes obtained by the procedure according to the invention to include such sequences in given proteins. This includes the addition of "labels" at the N- or C-terminal end (repetition of an antigenic peptide of 6 to 10 residues) serving to bind a monoclonal antibody, for purification by immunoaffinity or for identification in tissues.

As is apparent from the foregoing, the invention is in no way limited to those of its embodiments and modes of implementation and application which have just been described more explicitly; it embraces, on the contrary, all variants which may occur to the specialist in the field, without departing from the scope or the compass of the present invention.

---

We claim:

1. A method for polymerizing a nucleic acid sequence comprising:
    (a) providing a cloning vector containing a copy of a nucleic acid sequence to be polymerized and a suppressor tRNA gene,
        wherein the cloning vector of step (a) comprises restriction sites a, b, c, and d;
        the restriction site b is located in between the restriction sites a and c, and the restriction site c is located in between the restriction sites b and d;
        cleavage at the restriction site a gives an end a, cleavage at the restriction site b gives an end b, and cleavage at the restriction site d gives an end d;
        the end a and the end b are compatible ligation ends;
        the copy of step (a) is located in between the restriction sites a and b; and
        the suppressor tRNA gene is located in between the restriction sites c and d;
    (b) providing a cloning vector containing another copy of the nucleic acid sequence to be polymerized,
        wherein the cloning vector of step (b) comprises the restriction sites a, b, and d;
        the restriction site b is located in between the restriction sites a and d; and
        the copy of step (b) is located in between the restriction sites a and b;
    (c) cleaving the cloning vector of step (a) at the restriction sites a and d, thereby liberating a restriction fragment containing the copy of step (a) and the suppressor tRNA gene, and the ends a and d;
        wherein the copy of step (a) and the suppressor tRNA gene are located in between the ends a and d;
    (d) cleaving the cloning vector of step (b) at the restrictions sites b and d, thereby liberating a restriction fragment containing the copy of step (b), and the ends b and d;
        wherein the copy of step (b) is located in between the end b and the restriction site a;
    (e) ligating the end a of the restriction fragment of step (c) to the end b of the restriction fragment of step (d), and ligating the end d of the restriction fragment of step (c) to the end d of the restriction fragment of step (d), thereby forming a cloning vector containing the copy of step (a), the copy of step (b), and the suppressor tRNA gene, thereby polymerizing the nucleic acid sequence;
    (f) transforming, with the cloning vector of step (e), a bacterial strain having a mutation that is capable of being suppressed by the suppressor tRNA gene, thereby suppressing the mutation in the bacterial strain by the suppressor tRNA gene;
    (g) selecting the transformed bacterial strain, thereby selecting a bacterial strain containing the polymerized nucleic acid sequence;
    (h) isolating the cloning vector of step (e) from the selected transformed bacterial strain, thereby isolating the polymerized nucleic acid sequence; and
    (i) repeating steps (a) through (h) a finite number of times, wherein the cloning vector of (e) is used as the cloning vector of step (a).

2. The method of claim 1, wherein the restriction sites a and b are different.

3. The method of claim 1, wherein restriction sites a and b are not regenerated after ligating the end a of the restriction fragment of step (c) to the end b of the restriction fragment of step (d).

4. The method of claim 1, wherein the ends a and b are each blunt ends.

5. The method of claim 4, wherein:
    the restriction site a is Pvu II and the restriction site b is Eco RV;
    the restriction site a is Eco RV and the restriction site b is Pvu II;
    the restriction site a is Pvu II and the restriction site b is Hinc II;
    the restriction site a is Hinc II and the restriction site b is Pvu II;
    the restriction site a is Pvu II and the restriction site b is Sma I;
    the restriction site a is Sma I and the restriction site b is Pvu II;
    the restriction site a is Pvu II and the restriction site b is Sna BI;
    the restriction site a is Sna BI and the restriction site b is Pvu II;
    the restriction site a is Pvu II and the restriction site b is Ssp I;
    the restriction site a is Ssp I and the restriction site b is Pvu II;
    the restriction site a is Eco RV and the restriction site b is Hinc II;
    the restriction site a is Hinc II and the restriction site b is Eco RV;
    the restriction site a is Eco RV and the restriction site b is Sma I;
    the restriction site a is Sma I and the restriction site b is Eco RV;
    the restriction site a is Eco RV and the restriction site b is Sna BI;
    the restriction site a is Sna BI and the restriction site b is Eco RV;
    the restriction site a is Eco RV and the restriction site b is Ssp I;
    the restriction site a is Ssp I and the restriction site b is Eco RV;
    the restriction site a is Hinc II and the restriction site b is Sma I;
    the restriction site a is Sma I and the restriction site b is Hinc II;
    the restriction site a is Hinc II and the restriction site b is Sna BI;
    the restriction site a is Sna BI and the restriction site b is Hinc II;

the restriction site a is Hinc II and the restriction site b is Ssp I;

the restriction site a is Ssp I and the restriction site b is Hinc II;

the restriction site a is Sna I and the restriction site b is Sna BI;

the restriction site a is Sna BI and the restriction site b is Sma I;

the restriction site a is Sma I and the restriction site b is Ssp I;

the restriction site a is Ssp I and the restriction site b is Sma I;

the restriction site a is Sna BI and the restriction site b is Ssp I; or the restriction site a is Ssp I and the restriction site b is Sna BI.

6. The method of claim 1, wherein the ends a and b are each cohesive ends.

7. The method of claim 6, wherein:

the restriction site a is Eco RI and the restriction site b is Mun I;

the restriction site a is Mun I and the restriction site b is Eco RI;

the restriction site a is Apa LI and the restriction site b is Sfc I;

the restriction site a is Sfc I and the restriction site b is Apa LI;

the restriction site a is Bam HI and the restriction site b is Bcl I;

the restriction site a is Bcl I and the restriction site b is Bam HI;

the restriction site a is Bam HI and the restriction site b is Bgl II;

the restriction site a is Bgl II and the restriction site b is Bam HI;

the restriction site a is Bam HI and the restriction site b is Bst YI;

the restriction site a is Bst YI and the restriction site b is Bam HI;

the restriction site a is Sal I and the restriction site b is Xho I;

the restriction site a is Xho I and the restriction site b is Sal I;

the restriction site a is Nco I and the restriction site b is Bsp HI;

the restriction site a is Bsp HI and the restriction site b is Nco I;

the restriction site a is Nco I and the restriction site b is Afl III;

the restriction site a is Afl III and the restriction site b is Nco I;

the restriction site a is Xma I and the restriction site b is Age I;

the restriction site a is Age I and the restriction site b is Xma I;

the restriction site a is Ngo Ml and the restriction site b is Bsp EI;

the restriction site a is Bsp EI and the restriction site b is Ngo Ml;

the restriction site a is Xba I and the restriction site b is Nhe I;

the restriction site a is Nhe I and the restriction site b is Xba I;

the restriction site a is Xba I and the restriction site b is Avr II;

the restriction site a is Avr II and the restriction site b is Xba I;

the restriction site a is Xba I and the restriction site b is Spe I;

the restriction site a is Spe I and the restriction site b is Xba I;

the restriction site a is Bss HII and the restriction site b is Mlu I;

the restriction site a is Mlu I and the restriction site b is Bss HII;

the restriction site a is Bss HII and the restriction site b is Dsa I;

the restriction site a is Dsa I and the restriction site b is Bss HII;

the restriction site a is Bst BI and the restriction site b is Cla I;

the restriction site a is Cla I and the restriction site b is Bst BI;

the restriction site a is Bst BI and the restriction site b is Acc I;

the restriction site a is Acc I and the restriction site b is Bst BI;

the restriction site a is Bst BI and the restriction site b is Nar I;

the restriction site a is Nar I and the restriction site b is Bst BI;

the restriction site a is Bst BI and the restriction site b is Psp 1406 I;

the restriction site a is Psp 1406 I and the restriction site b is Bst BI;

the restriction site a is Pst I and the restriction site b is Nsi I; or the restriction site a is Nsi I and the restriction site b is Pst I.

8. The method of claim 1, wherein restriction sites c and d are different than restriction sites a and b.

9. The method of claim 1, wherein the suppressor tRNA gene does not contain restriction site c or d.

10. The method of claim 1, wherein the restriction sites b and c overlap.

11. The method of claim 1, wherein the restriction site a is a Xho I restriction site, the restriction site b is a Sal I restriction site, the restriction site c is a Hind III restriction site, and the restriction site d is a Xba I site.

12. The method of claim 1, wherein the suppressor tRNA gene is an ochre suppressor tRNA gene, an opal suppressor tRNA gene, a frameshift suppressor tRNA gene, or an amber suppressor tRNA gene.

13. The method of claim 1, wherein the bacterial strain is a strain of *Escherichia coli*.

14. The method of claim 1, wherein the bacterial strain carries an amber mutation in an essential gene and in a reporter gene.

15. A method for the preparation of a ladder containing polymerized DNA sequences, wherein the ladder comprises a first polymerized DNA sequence and a second polymerized DNA sequence;

the first polymerized DNA sequence contains a different number of copies of a nucleotide sequence than the second polymerized DNA sequence; and the method comprises:

preparing each polymerized DNA sequence by the method of claim 1; and cleaving each cloning vector of step (e) at restriction sites a and b, thereby preparing the ladder containing the polymerized DNA sequences.

16. The method of claim 15 comprising the additional step of adding to the ladder a DNA sequence containing one copy of the nucleotide sequence.

17. A method for preparing a vector or a genome containing a polymerized DNA sequence comprising:

preparing the polymerized DNA sequence by the method of claim 1;

isolating the polymerized DNA sequence from the cloning vector of step (e); and attaching the isolated polymerized DNA sequence to the vector or the genome, thereby preparing the vector or the genome containing the polymerized DNA sequence.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

```
TCGACTATGG   GCGCAGCGTC   AATGACGCTG   ACGGTACAGG   CC                    4 2
```

( 2 ) INFORMATION FOR SEQ ID NO:2:

( i ) SEQUENCE CHARACTERISTICS:
        ( A ) LENGTH: 42 base pairs
        ( B ) TYPE: nucleic acid
        ( C ) STRANDEDNESS: single (D) TOPOLOGY: linear (xi) SEQUENCE DESCRIPTION: SEQ ID NO:2:

TCGAGGCCTG TACCGTCAGC GTCATTGACG CTGCGCCCAT AG                42